(12) United States Patent
Vult Von Steyern

(10) Patent No.: US 8,834,161 B2
(45) Date of Patent: Sep. 16, 2014

(54) ZIRCONIUM DIOXIDE BASED PROSTHESES

(75) Inventor: Per Vult Von Steyern, Malmo (SE)

(73) Assignee: Innovationspatent Sverige AB, Lund (SE)

( * ) Notice: Subject to any disclaimer, the term of this patent is extended or adjusted under 35 U.S.C. 154(b) by 0 days.

(21) Appl. No.: 13/254,585

(22) PCT Filed: Mar. 4, 2010

(86) PCT No.: PCT/SE2010/050249
§ 371 (c)(1),
(2), (4) Date: Sep. 19, 2011

(87) PCT Pub. No.: WO2010/101523
PCT Pub. Date: Sep. 10, 2010

(65) Prior Publication Data
US 2012/0022648 A1    Jan. 26, 2012

(30) Foreign Application Priority Data

Mar. 4, 2009   (SE) ...................................... 0900281

(51) Int. Cl.
*A61C 13/08*   (2006.01)
*B25B 1/00*   (2006.01)

(52) U.S. Cl.
USPC ...................................... 433/202.1; 264/681

(58) Field of Classification Search
USPC ................ 433/201.1, 202.1, 212.1, 218, 223; 264/16–20, 681; 216/97, 11, 33, 34, 216/83; 428/542.8, 697; 29/896.11; 623/11, 623/12, 12.11
See application file for complete search history.

(56) References Cited

U.S. PATENT DOCUMENTS

| | | | | |
|---|---|---|---|---|
| 2,948,018 | A | * | 8/1960 | Hintermann et al. .......... 425/567 |
| 4,604,059 | A | * | 8/1986 | Klaus et al. ................ 433/217.1 |
| 5,077,132 | A | * | 12/1991 | Maruno et al. ................ 428/426 |
| 5,914,086 | A | * | 6/1999 | Hermann et al. ............. 264/430 |
| 2002/0006532 | A1 | * | 1/2002 | Robin ........................... 428/697 |
| 2008/0241551 | A1 | * | 10/2008 | Zhang et al. .................. 428/428 |

(Continued)

FOREIGN PATENT DOCUMENTS

| | | |
|---|---|---|
| DE | 102004050202 | 4/2006 |
| DE | 102006037067 | 2/2008 |

(Continued)

OTHER PUBLICATIONS

Zhang et al. Dental Materials 2009, vol. 25, p. 781-790, "Graded structures for damage resistant and aesthetic all-ceramic restorations."

(Continued)

*Primary Examiner* — Heidi M Eide
*Assistant Examiner* — Matthew Saunders
(74) *Attorney, Agent, or Firm* — Brooks Kushman P.C.

(57) ABSTRACT

A process for the manufacture of a zirconium oxide prosthesis, the zirconium oxide being stabilized, which process includes the following steps: a) compacting a zirconium oxide powder at a pressure of at least 45 MPa to an object of a desired form, b) impacting an etchable medium into the surface, c) optionally working the object to a final shape, d) sintering the body at a temperature of above 1170° C. to transfer zirconium oxide into a tetragonal crystalline structure, and e) etching the etchable medium using hydrofluoric acid to remove the medium and impart a micromechanical retention surface. A prosthesis prepared by this process is also disclosed.

20 Claims, 2 Drawing Sheets

(56) References Cited

U.S. PATENT DOCUMENTS

2008/0261178 A1* 10/2008 Homann et al. ........... 433/201.1
2010/0003630 A1   1/2010 Yamashita et al.
2011/0136653 A1   6/2011 Koebel et al.

FOREIGN PATENT DOCUMENTS

| EP | 0631995 | | 1/1995 |
|----|---------|---|--------|
| EP | 1093769 | * | 4/2001 |
| EP | 1777206 A1 | | 4/2007 |
| EP | 1982670 A1 | | 10/2008 |
| JP | 10513166 | | 12/1998 |
| WO | 9623481 | | 8/1996 |
| WO | 2008009272 A1 | | 1/2008 |
| WO | 2008013099 | | 1/2008 |
| WO | 2008060451 | | 5/2008 |

OTHER PUBLICATIONS

Extended European Search Report for PCT/SE2010/050249, Completed on Jul. 4, 2012, 11 Pages.
Japanese Office Action for JP Application No. 2011-552911, Dated Apr. 9, 2013, 6 pages.
Aboushelib, M.N. et al, "Selective Infiltration-Etching Technique for a Strong and Durable Bond of Resin Cements to Zirconia-Based Materials," The Journal of Prosthetic Dentistry, v. 98, Issue 5, Nov. 2007, pp. 379-388.
Hirata, T. et al., "Thermal Decomposition of Urea-Formaldehyde and Melamine-Formaldehyde Resins I. Weight Loss of Urea-Formaldehyde Resin with Healing," J. Appl. Polymer Sci., v. 12-4 (1986), pp. 279-286, English Summary.
International Search Report for PCT/SE2010/050249, Completed by the Swedish Patent Office on May 26, 2010, 4 Pages.

* cited by examiner

US 8,834,161 B2

ZIRCONIUM DIOXIDE BASED PROSTHESES

CROSS-REFERENCE TO RELATED APPLICATION

This application is the U.S. national phase of PCT Appln. No. PCT/SE2010/050249 filed Mar. 4, 2010 which claims priority to Swedish application 0900281-7 filed Mar. 4, 2009, the disclosures of which are incorporated in their entirety by reference herein.

TECHNICAL FIELD

The present invention relates to zirconium dioxide (zirconia) based prostheses, and in particular to a method for obtaining a bondable surface onto a zirconium dioxide surface.

BACKGROUND OF THE INVENTION

All-ceramic restorations have become a choice for dentists, especially concerning reconstructions based on partially or fully stabilized tetragonal zirconium dioxide. While pure zirconium dioxide has unfavourable mechanical properties, it is possible to control the material by doping it with a stabilising oxide, thus gaining favourable toughness, superior to other dental ceramics. Two currently available zirconia-based ceramics for dental use are partially-stabilized zirconia (PSZ) and yttria-stabilized tetragonal zirconia polycrystals (Y-TZP). Stabilized zirconia can be processed either by soft machining of green-stage or presintered blanks followed by sintering at temperatures varying between 1350° C.-1550° C., or by hard machining of completely sintered blanks. With only one exception known to the authors, all zirconia brands on the market currently are based on Y-TZP. Stabilization of the zirconium dioxide can be made using yttria, magnesium oxide, calcium oxide or cesium oxide. In the case of an addition of yttria this will be added in an amount of 7.5 to 9.5, preferably 8% by weight.

Y-TZP will show different crystal structures depending on temperature. At ambient temperature and up to 1170° C. the crystals have a monocline structure. Between 1170° C. and 2370° C. a phase transformation occurs and it is transformed into a tetragonal structure. Above 2370° C. the material will become converted to a cubic structure. When there is a transformation from tetragonal to monocline structure an increase of volume of the material takes place with about 4.5% which may lead to undesired crack formation within the material. By adding stabilizing oxides, such as CaO, MgO, $Y_2O_3$ or $CeO_2$, as mentioned above, the tetragonal phase will become controlled at ambient temperature, a phase which otherwise will not occur at ambient temperature. Y-TZP inhibits actively cracks. When a crack starts to propagate a local tension initiated phase transformation from tetragonal to monocline phase, which leads to an increase of the volume of the crystal structure with 1 to 3% and a directed compressive stress will be obtained which halts the propagating crack.

A number of clinical studies published recent years are based on cemented Y-TZP reconstructions where the cementation techniques rely mainly on macro-mechanical retention. In those cases, the geometry of the supporting teeth gives retention rather than a direct bond between the different structures included (the ceramic material, the cement, dentine and enamel). The geometry needed to enable such retention, however, presupposes tooth preparation with often a substantial tissue loss of tooth material, enamel and dentine, as a consequence. By utilizing bonding technique it would be possible to decrease the need for substantial tooth preparation, thus preserving tooth substance.

The main reason for still being dependent on traditional retentive technologies instead of bonding techniques when using Y-TZP is that the composition and physical properties of the polycrystalline ceramic differ substantially from those of silica based ones. While silica-based ceramics allow for both a micromechanical and chemical bond, the Y-TZP does not include a glass phase. The surface is chemically inert and in most cases show a microstructure that does not allow for micromechanical retention without utilizing some kind of surface modification.

Hydrofluoric etching creates a rough, mainly crystalline surface with pits and micro-lacunas when used to modify the seating surface on dental porcelain and dental glass ceramics. This created surface topography enhances retention by interlocking the luting agent, creating a micromechanical bond. The surface glass is almost completely removed, but the crystal phases are not pronouncedly affected by the acid, and hence remain substantially unchanged after etching. A small portion of glass remnants in the surface, contribute to enhance a chemical bond between the luting agent and the ceram.

The surface of a polycrystalline ceram (e.g. Y-TZP) on the other hand, remains completely unchanged after etching, as the acid does not react with the chemically stable crystals, as previously mentioned.

The interest in a finding a method to obtain strong and reliable bonds between polycrystalline ceramics and a bonding system seem obvious when reviewing the literature. Several methods of surface modifications are highlighted by the current research as for instance silanisation, sandblasting, sandblasting in combination with silanisation, silica coating, tribochemical silica coating, MDP-silane coupling agent surface treatment, selective infiltration etching and different combinations of the methods. Furthermore, several studies have investigated and compared different bonding systems and combinations of primers and luting agents. Novell bonding theories have also been considered, e.g. that chemical bond actually can be achieved to Y-TZP. Still, the literature gives at hand that establishing a strong and reliable bond between Y-TZP and tooth structure, or per definition between Y-TZP and a bonding component is difficult and unpredictable.

Yttrium oxide stabilized tetragonal polycrystalline zirconium oxide (Y-TZP) is an oxide ceramic material having mechanical properties which differs from other oxide ceramic materials. The bending strength of Y-TZP is between 900 and 1200 MPa and the fracture toughness is between 6 and 8 $MPa*m^{0.5}$, which makes the material suitable as a core material for all ceramic replacements. Outside the core material one or more layers of porcelain is/are added. The porcelain has a considerably lower structural strength, 70 to 120 MPa but is often needed to obtain an esthetically acceptable appearance.

In some papers it is stated that adhesive cementing can be made when the inner surfaces of constructions made of an oxide ceramic material has a micromechanical retention which has been created at the processing. When all ceramic constructions are cut out of a raw material, the cutter leaves a certain structure in the surface, e.g., an inner surface to be applied onto a reduced tooth structure, i.e., onto a dentine structure. This can only be applied at a subtractive production when one cuts the whole replacement from a solid block. At an additive production, one press oxide ceramic powder against a prefabricated surface and then the outer contours are cut and sintered whereby there is no unevennesses by the cutter on the inner surfaces of the construction and thereby limits the possibility of micromechanical retention.

SUMMARY OF THE PRESENT INVENTION

The present invention aims at solving this problem by providing a surface on the zirconium dioxide object, which surface can be bond and retained to a second object such as a bone structure, enamel structure or dentine structure as well as a ceramic structure.

More particularly the present invention relates to a process for the manufacture of a zirconium oxide prosthesis, said zirconium oxide being stabilized, said method comprising the following steps:
a) compacting a zirconium oxide powder at a pressure of at least 45 MPa to an object of a desired form,
b) impacting an etchable medium into the surface,
c) optionally working the object to a final shape,
d) sintering the body at a temperature of above 1170° C. to transfer zirconium oxide into a tetragonal crystalline structure, and
e) etching the etchable medium using hydrofluoric acid to remove the medium and impart a micromechanical retention surface.

According to some embodiments of the invention, which may be a preferred embodiment in some situations, the etchable medium comprises polymer particles or is constituted by polymer particles. Such may be formed by a cured and ground urea formaldehyde resin having a particle size of 50 μm.

According to some embodiments of the invention, which may be a preferred embodiment in some situations, the etchable medium comprises or is constituted by glass particles. When glass particles are used, it may in some embodiments be preferably to use a silica glass having a particle size of 0 to 40 μm.

According to some embodiments of the invention, which may be a preferred embodiment in some situations, the sintering temperature is 1300 to 1600° C. In some situations it may be preferred that the sintering temperature is 1350 to 1550° C.

According to some embodiments of the invention, which may be a preferred embodiment in some situations, the zirconium oxide is stabilized with one or more of the compounds selected from the group consisting of the group yttrium oxide, magnesium oxide, calcium oxide and cesium oxide.

According to some embodiments of the invention, which may be a preferred embodiment in some situations, the compacting step a) is carried out at a pressure of 45 to 150 MPa.

According to some embodiments of the invention, which may be a preferred embodiment in some situations, the compacting step a) is carried out using a cold isostat pressing.

According to some embodiments of the invention, which may be a preferred embodiment in some situations, the compacting step a) is carried out using a mechanical uniaxial pressure.

According to some embodiments of the invention, which may be a preferred embodiment in some situations, the compacting step a) is carried using a pressure cuvette.

According to some embodiments of the invention, which may be a preferred embodiment in some situations, the etching step e) is followed by a rinsing step f), wherein an organic or inorganic acid and/or water is used. In some situations it may be preferred to use a phosphoric acid.

According to some embodiments of the invention, which may be a preferred embodiment in some situations, a hydrofluoric acid having a concentration of 5 to 15% is used in the etching step e).

According to some embodiments of the invention, which may be a preferred embodiment in some situations, the etchable medium is contacted with the hydrofluoric acid for a time period of 1 to 10 min, or in some situations for a time period of 1 to 6 min, or preferably 1 to 3 min.

In a preferred embodiment of the invention the body is obtained using an additive forming process.

In a preferred embodiment of the invention the body is obtained using a subtractive forming process.

In accordance with a further aspect of the invention it relates to a prosthesis prepared in accordance with the process of the invention and consisting of a pre-compacted stabilized zirconium oxide body, being optionally shaped, sintered and/or etched.

Within the framework of this disclosure prosthesis is meant to mean any dental prosthesis and/or any ceramic implant used for reconstruction of a body or to carry any aid device implanted in the body such as, but not limited to, cochlear devices, knee prostheses and hip joint prostheses.

The invention is further described below, with reference to the drawings which illustrate the invention.

As mentioned above FIG. 1 shows a cast 1 of a dentin core. This dentin core has been designed prior to casting in order to meet maximum bonding ability during the subsequent restoration work. The cast is prepared to provide for an additive forming.

Figure 1:
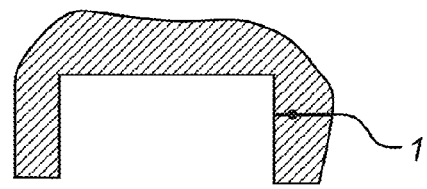
FIG. 1 shows a cast of a shaped dentin core being part of a molar tooth.
Figure 2:
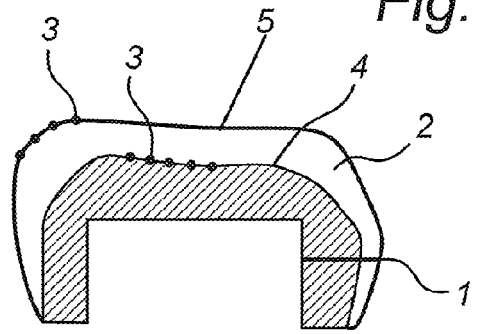
FIG. 2 shows the cast of FIG. 1 onto which a Y-TZP powder has been compacted.

As mentioned above FIG. 2 shows the cast 1 as shown in FIG. 1 provided with a compacted Y-TZP body 2, whereby glass beads 3 have been added to the dentin interface 4 as well as to the future porcelain (veneer) interface 5. It shall be noted that the glass beads are present in the mere interface although drawing indicates a coarser layer. When it comes to layer 5, this is not necessary in most cases as the porcelain is burnt onto the ceram oxide surface, thereby forming a chemical bond of high quality. In the cases the surface here having the layer 5 is to be worked on, there is no need for any application of glass beads.

Figure 3:
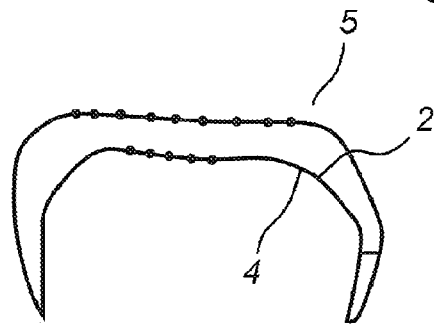
FIG. 3 shows the pre-sintered, compacted Y-TZP body

As mentioned above FIG. 3 shows the presintered or compacted Y-TZP body 2 with its layers 4 and 5 of glass beads prior to etching. The compacted body 2 can in this state be easily worked. The tool weariness increased 10-fold after final sintering.

Figure 4:
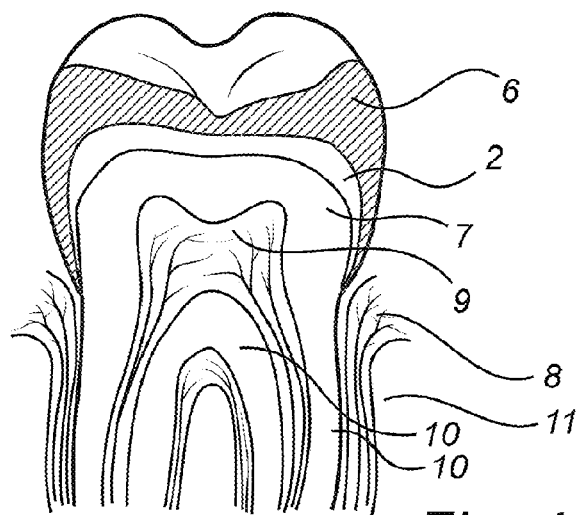
FIG. 4 shows the restored tooth with an enamel veneer, a Y-TZP central body, and the dentin core.

As mentioned above FIG. 4 shows a restored tooth with a porcelain veneer 6 to mimic a natural enamel surface and casted in accordance with mold prepared after the original tooth, the sintered and etched Y-TZP body 2 added onto a dentin core 7 using a resin cement of conventional type, such as any of those mentioned in the above description. The gum is indicated with 8 and the pulp 9, the cementum 10 and the jawbone 11.

The invention will be described more in detail in the following with reference to a number experiments carried out. Thus a prosthesis is prepared using the process of the invention, and is tested with regard to its retention by means of cementing to a feldspar body.

Materials and Methods

In this study, forty eight pairs of specimens were fabricated—one Y-TZP cylinder and one block made of porcelain that were to be adhesively luted together using a bonding system. The specimens differed in two ways—depending on the cementation surface of the Y-TZP cylinder (three different surfaces were to be tested) and depending on which bonding system used (two different systems were to be tested). Consequently, the 48 specimens constituted six subgroups, as described in FIG. 1.

Manufacture of the Y-TZP Cylinders

A special dry-press punching tool made of brass and stainless steel was made for the fabrication of the Y-TZP cylinders. The cylinder having a height of 18 mm and a through hole of 6 mm in diameter was manufactured. A steel rod having a diameter of 6 mm and a length of 19 mm was prepared to fit into the through hole.

The bottom punch surface of the press-tool that were to define the cementation surface of the Y-TZP cylinders, was adjusted prior to compaction by applying a thin layer of one of two different medium onto the pressing surface of the steel rod. Subsequently, the tool was filled with 33 grams of Y-TZP granulated powder (Procera Zirconia, Nobel Biocare™ AB, Gothenburg, Sweden) that were mechanically, uniaxially compressed with 45 to 150 MPa using a cuvette press (Pugliese 2 61, Cuneo, Italy). A 40 μm sieve was used to sieve the different media which was to have a particle size of 0 to 40 μm. The measure of the ready-pressed cylinders was 6 mm in diameter and 4 mm in height. The media I and II were applied in such an amount as to cover the surface to 50 to 100%. The media I had a particle size of 1 to 40 μm. Medium I consisted of glass beads, and medium II consisted of polymer beads of cured and ground urea formaldehyde resin and had a particle size of 50 μm. Both media were of a quality used for blasting purposes.

All Y-TZP cylinders were sintered in a sintering oven (Everest Therm 4180, KaVo Everest®, Biberach, Germany) according to the manual of the producer of the oxide ceramic material, although with a certain modification as the cooling time had not been given Instead the recommendations given by the producer of the sintering oven was followed. The final sintering temperature was 1500° C. The measures of the cylinders after sintering of the Y-TZP were a diameter of 5 mm and a height of 3 mm.

The three groups differed depending on different surface-modifications as described below:

Control: No medium was added to the bottom punch prior to compaction.
Surface 1: The bottom punch surface was covered with a thin layer of polymer granules, with a particle size of 40 μm or less, prior to compaction.
Surface 2: The bottom punch surface was covered with a thin layer of glass granules, with a particle size of 40 μm or less, prior to compaction.

The dimensions of the cylinders were 6 mm in diameter and 4 mm in height after compaction. All cylinders, independent of group, were finally sintered in a sintering furnace (Everest Therm 4180, KaVo Everest®, Biberach, Germany) according to the ceram-manufacturers' instructions with a cooling phase according to the furnace manufacturer's instructions. The final dimensions of the cylinders were 5 mm in diameter (range: 4.97 mm-5.11 mm) and 3 mm in height. The shrinkage ranged between 17.4% and 20.7%.

Manufacture of the Feldspathic Porcelain Blocks

Porcelain blocks were manufactured by using a specially made brass mold also described above.

Porcelain (Duceram® Plus dentin A3.5, Degudent, Hanau-Wolfgang, Germany) was shaped to a block in the mould and fired in a porcelain furnace (Programat P500, Ivoclar Vivadent, Schaan, Liechtenstein). Two dentine firings and one glaze firing were performed according to the manufacturers' instructions. After firing, the blocks were giving their final shape by grinding with a 120 grit paper (Buehler-Met® II, Buehler Ltd., Lake Bluff, Ill., USA) to enable fixation during the test. All grinding was done carefully with water cooling.

Pre-Treatment of the Cementation-Surfaces

The cementation-surface of both the porcelain blocks and all the Y-TZP cylinders were treated with 9.6% hydrofluoric acid (Top Dent 9.6%, DAB Dental, Upplands Väsby, Sweden), thoroughly rinsed, cleaned with 35% phosphoric acid (Ultra-Etch 35%, Ultradent products, Inc, South Jordan, Utah, USA) and again thoroughly rinsed according to the manufacturers' recommendations.

Cementation of the Cylinder Discs and Blocks

Subsequently the cylinder discs and porcelain blocks were treated with corresponding silane and adhesive cement, according to respective manufacturer's recommendation. Before cementation, the cylinders from the three groups (n=16, a total number of 48) with different surface relief and the feldspathic porcelain blocks (n=48) were randomly divided into six subgroups (n=8). Two different bonding systems was used, Variolink®II (Ivoclar Vivadent AG/FL-9494 Schaan/Liechtenstein) and Panavia™ F (KURARAY MEDICAL INC/Okayama 710-8622/Japan).

Figure 5:
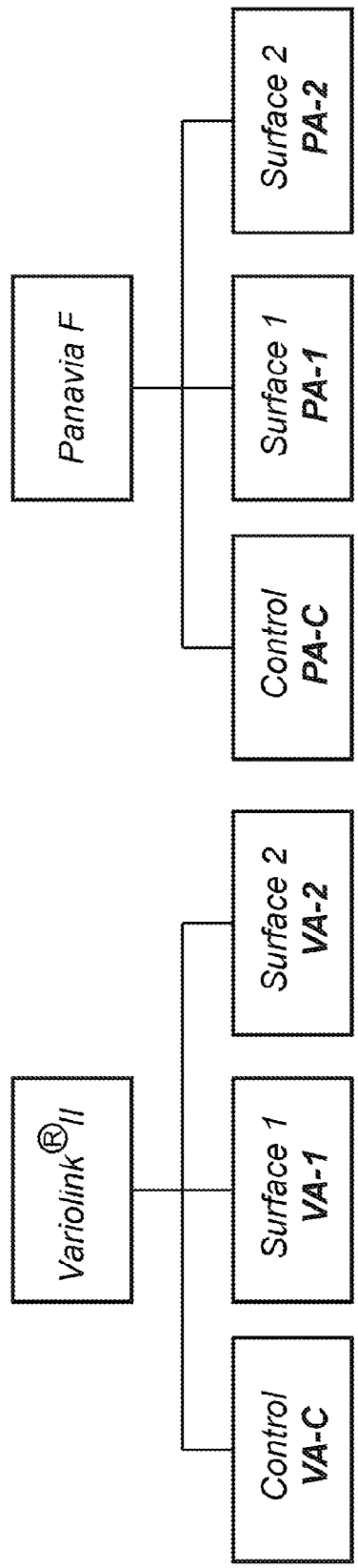
FIG. 5 shows an overview of the subgroups where Variolink®II and Panavia F® are the bonding systems used.

Schematic overview of the grouping of test bodies is given in FIG. 5.

The cementations with respective bonding system were carried out according to table 1.

TABLE 1

| Cementation record. | | | | | |
|---|---|---|---|---|---|
| Systems with belonging components | Surfaces | Application time | Working time | Rinsing (H$_2$O) | Air blasting |
| Variolink ®II | | | | | |
| Hydrofluoric acid | F + Z | 2 min | 2 min | 2 min | 15 sec |
| Phosphoric acid | F + Z | 5 sec | 2 min | 1 min | 15 sec |
| Monobond S | F + Z | 5 sec | 60 sec | — | 5 sec |
| Heliobond | F | 5 sec | 5 sec | — | 5 sec |

TABLE 1-continued

Cementation record.

| | | Mixing time | Curing time |
|---|---|---|---|
| Variolink ®II base + catalyse Liquid strip | F + Z | 10 sec | 4 × 20 sec + 60 sec 1 min |

| Systems with belonging components | Surfaces* | Application time | Working time | Rinsing (H$_2$O) | Air blasting |
|---|---|---|---|---|---|
| Panavia ™F | | | | | |
| Hydrofluoric acid | F + Z | 2 min | 2 min | 2 min | 15 sec |
| Phosphoric acid | F + Z | 5 sec | 2 min | 1 min | 15 sec |
| Metal Primer | Z | 5 sec | 5 sec | — | 5 sec |
| Clearfil ™ Porclain bond activator + Clearfil ™ SE Bond primer | F | 5 sec | 5 sec | — | 5 sec |

| | | Mixing time | Curing time |
|---|---|---|---|
| Panavia ™F base + catalyze Panavia ™F Oxyguard | F + Z | 20 sec | 4 × 20 sec + 60 sec 1 min |

F is Feldspathic porcelain; Z is Y-TZP

The cylinder discs were luted to the feldspathic blocks with an alignment apparatus that applied a seating load of 15 N during polymerisation. The apparatus ensured a standardised seating load and that the axes of the cylinder disc were perpendicular to the surface of the block. Excess resin was removed from the margin using disposable brushes (top Dent, DAB Dental AB, Sweden). An oxygen-blocking gel was used according to the manufacturers' instructions (Table 1). The cements were light-cured with a dental curing lamp (Ivoclar Vivadent bluephase, Schaan, Liechtenstein) with a polymerisation light intensity of 1600 mW/cm$^2$, for 20 seconds from four directions, 90° apart and additionally 60 seconds with the seating load removed. Any excess resin was removed with a surgical blade (AESCULAP® no. 12, AESCULAP AG & CO, Tuttlingen, Germany) after completed polymerisation. In a final step, the specimens were rinsed with water for one minute to remove the oxygen-blocking gel remnants and then storied for 10 hours in a humid environment.

Analysis of the Surfaces

During the manufacturing of the specimens, after pressing, sintering and cementation a representative specimen from each group were examined with two different types of microscope, (WILD M3, WILD HEERBRUGG, Herrbrugg, Switzerland and Leica DM 2500M Leica Microsystems CMS, Wetzlar, Germany) at ×31 respective ×50 magnification. The fracture surfaces from all the specimens that were shear bond strength tested were also examined. The surfaces were photographed with a digital camera (Olympus DP12, Tokyo, Japan) connected to respective microscope. During analyze and photo documentation with the microscope WILD M3, an external light (Volpi Intralux® 5000, Schlieren, Switzerland) was used.

Pre-Treatment

All the specimens underwent 5000 thermocycles in a specially constructed thermocycling device. The specimens were cycled in two baths, one at 5° C. and one at 55° C. Each cycle lasted 60 seconds: 20 seconds in each bath and 10 seconds for transferring between the baths.

Shear Bond Strength

The shear bond strength was determined in a universal testing machine (Instron model 4465, Instron® Canton, Mass., USA) with a knife-edged blade parallel to the bonded surfaces according to previous studies. The feldspathic blocks were placed in a brass holder fixated in the testing machine to maintain their position during testing. The cross head speed was 0.5 mm/min. The load at the point of debonding or the feldspathic blocks fractured was recorded, (Philips PM 8010, Bobigny, France) and shear bond strength was calculated:

$$C = \frac{F}{\pi r^2}$$

wherein C stands for the bond strength (MPa), F stands for the load (N) at debonding or fracture, and r is the radian in mm of the cemented area in mm$^2$.

The mean value of the retention strength as well as standard deviation of the respective groups was as highest for group VA-1 35.56 (+5.99 MPa) followed by the group VA-2 with a value of 34.81 (+7.40 MPa). The group PA-1 had a mean value of 26.39 (+4.02 MPa), followed by the PA-2 group with the value 30.13 (+3.98 MPa). The two lowest values were related to the groups VA-Z and PA-Z, 22.00 (+4.32 MPa) as well as 17.83 (+3.3 8 MPa) respectively, see Table 2.

TABLE 2

Mean value, standard deviation, maximum and minimum values, as well as the number of adhesive and cohesive fractures, respectively, of the respective group at shear.

| Respective group | Mean value | SD | Max value | Min value | Adhesive F | Cohesive F |
|---|---|---|---|---|---|---|
| Group VA-1 | 35.56 | ±5.99 | 42.56 | 25.83 | 2 | 6 |
| Group VA-2 | 34.81 | ±7.40 | 44.03 | 23.93 | 0 | 8 |
| Group VA-Z | 22.0 | ±4.32 | 28.92 | 16.71 | 8 | 0 |
| Group PA-1 | 26.39 | ±4.02 | 32.40 | 21.83 | 2 | 6 |

TABLE 2-continued

Mean value, standard deviation, maximum and minimum values, as well as the number of adhesive and cohesive fractures, respectively, of the respective group at shear.

| Respective group | Mean value | SD | Max value | Min value | Adhesive F | Cohesive F |
|---|---|---|---|---|---|---|
| Group PA-2 | 30.13 | ±3.98 | 36.47 | 25.28 | 4 | 4 |
| Group PA-Z | 17.83 | ±3.38 | 25.00 | 13.23 | 8 | 0 |

SD = Standard deviation
Adhesive F = fracture between the interfaces between feltspat porcelain and Y-TZP
Cohesive F = fracture in the feltspat porcelain There was no significant difference between the group VA-1 and the groups VA-2 and PA-2 (p>0.05). However, there is a significant difference vis-à-vis PA-1 (p<0.01) and the other groups where VA-1 in the relation showed a higher bonding strength (p<0.001). The group VA-2 showed a higher significant bonding strength vis-à-vis the groups VA-Z, PA-Z (p<0.001), and PA-1 (p<0.05). There was no significant difference in bonding strength between VA-Z, PA-Z, and PA-1 (p>0.05). Between the groups VA-Z 34.81 (+7.40 MPa) and PA-2 30.13 (+3.98 MPa) there was a significantly higher difference in bonding strength (p<0.05). PA-1 had a significantly higher bonding strength compared with the group PA-Z (p<0.05) but there was no statistical significant difference to the group PA-2 (p>0.05). The group PA-2 showed a significantly higher bonding strength than the group PA-Z (p<0.001), see Table 3.

TABLE 3

Table showing statistically significant differences between the groups, with regard to bonding strength.

| Respective group | VA-1 | VA-2 | VA-Z | PA-1 | PA-2 | PA-Z |
|---|---|---|---|---|---|---|
| VA-1 | n/a | NS | *** | ** | NS | *** |
|  |  | 1.000 | 0.000 | 0.009 | 0.282 | 0.000 |
| VA-2 | NS | n/a | *** | * | NS | *** |
|  | (1.000) |  | 0.000 | 0.021 | 0.442 | 0.000 |
| VA-Z | *** | *** | n/a | NS | * | NS |
|  | 0.000 | 0.000 |  | 0.531 | 0.030 | 0.554 |
| PA-1 | ** | * | NS | n/a | NS | * |
|  | 0.009 | 0.021 | 0.531 |  | 0.678 | 0.018 |
| PA-2 | NS | NS | * | NS | n/a | *** |
|  | 0.282 | 0.442 | 0.030 | 0.678 |  | 0.000 |
| PA-Z | *** | *** | NS | * | *** | n/a |
|  | 0.000 | 0.000 | 0.554 | 0.018 | 0.000 |  |

NS = No significant difference
*** P~0.001
** P~0.01
* P~0.05
n/a = not available

TABLE 4

Table showing significant differences between the groups with regard to fractures, adhesive or cohesive

| Respective group | VA-1 | VA-2 | VA-Z | PA-1 | PA-2 | PA-Z |
|---|---|---|---|---|---|---|
| VA-1 | n/a | NS | ** | NS | NS | ** |
|  |  | 0.5/1.0 | 0.003/0.007 | 0.7/1.0 | 0.3/0.6 | 0.003/0.007 |
| VA-2 |  | n/a | *** | NS | NS | *** |
|  |  |  | 0.0007/0.001 | 0.5/1.0 | 0.14/0.28 | 0.0007/0.001 |
| VA-Z |  |  | n/a | ** | (*) | NS |
|  |  |  |  | 0.003/0.007 | 0.04/0.08 | 1.0/1.0 |
| PA-1 |  |  |  | n/a | NS | ** |
|  |  |  |  |  | 0.3/0.6 | 0.003/0.007 |
| PA-2 |  |  |  |  | n/a | (*) |
|  |  |  |  |  |  | 0.038/0.07 |
| PA-Z |  |  |  |  |  | n/a |

NS = No significant difference
*** P~0.001,
** P~0.01,
* P~0.05
n/a = not available From the data obtained, mean and standard deviation for each group were calculated. One-way ANOVA, Tukey's test was used to determine the differences between the groups. Fisher's Exact Probability Test was also used to determine the failure modes in the debonded area in each group. The level of significance was set to α≥0.05. Thereby it was determined that the bond between the zirconium dioxide treated with glass beads and with hydrofluoric acid showed a shear strength of at least 25 MPa.

Using Cad-Cam (Computer aided design—Computer aided manufacturing) one can produce all ceramic inner constructions of presintered (pre-compacted) and sintered zirconium oxide, such as Y-TZP. Thus Maryland bridges used within dentistry can be prepared, molar teeth can be prepared where no porcelain veneer is added, or more forward presented teeth where a porcelain veneer is added. The products can be made using an additive formation/design, where the body is prepared using a mold of a preselected—preshaped design, such as molds obtained after casting such as in a polymer material, generally used within dentistry.

Replacements made of Y-TZP can be cemented using conventional technique, i.e., zinc phosphate or glass ionomer cement. When using resin cement at the cementing the bond between Y-TZP and the enamel or dentine is not as trustworthy as using the conventional cements. This is due to the fact that there is a glass phase in the silica based ceram which can become etched.

The invention claimed is:

1. A process for manufacturing a zirconium oxide prosthesis, the zirconium oxide being stabilized, comprising the steps of:
   a) compacting a zirconium oxide powder at a pressure of at least 45 MPa to form an object and simultaneously impacting an etchable medium into a surface of the object;
   b) sintering the object at a temperature above 1170° C. and below 2370° C. to transfer zirconium oxide into a tetragonal crystalline structure; and
   c) etching the etchable medium using hydrofluoric acid to remove the etchable medium and impart a micromechanical retention surface.

2. The process of claim 1, wherein the etchable medium is polymer particles.

3. The process of claim 1, wherein the etchable medium is glass particles.

4. The process of claim 1, wherein the sintering temperature is 1300 to 1600° C.

5. The process of claim 1, wherein the zirconium oxide is stabilized with one or more of compounds selected from the group consisting of yttrium oxide, magnesium oxide, calcium oxide, cesium oxide, and combinations thereof.

6. The process of claim 1, wherein the compacting step a) is carried out at a pressure of 45 to 150 MPa.

7. The process of claim 1, wherein the compacting step a) is carried out using a cold isostat pressing.

8. The process of claim 1, wherein the compacting step a) is carried out using a mechanical uniaxial pressure.

9. The process of claim 1, wherein the compacting step a) is carried using a pressure cuvette.

10. The process of claim 1, wherein the etching step c) is followed by a rinsing step with a component selected from the group consisting of an organic, inorganic acid, water, and combinations thereof.

11. The process of claim 1, wherein the hydrofluoric acid in the etching step c) takes place at a concentration of about 5-15% and the etching medium is contacted with the hydrofluoric acid for a time period of about 1 to 3 minutes.

12. The process of claim 1, wherein the object is obtained using an additive forming process.

13. The process of claim 1, wherein the object is obtained using a subtractive forming process.

14. The process of claim 1, further comprising a shaping step between the compacting step a) and the sintering step b), wherein the object is worked in a final shape.

15. The process of claim 1, wherein the etching step c) forms pits or micro-lacunas on the surface of the object.

16. A process for manufacturing a zirconium oxide prosthesis, the zirconium oxide being stabilized, comprising the steps:
   a) compacting a zirconium oxide powder and stabilizing oxides selected from the group consisting of yttrium oxide, magnesium oxide, calcium oxide and cesium oxide, wherein the compacting is at a pressure of 45 to 150 MPa to form an object and simultaneously impacting an etchable medium into a surface of the object, the etchable medium is selected from the group consisting of polymer particles, glass particles and combinations thereof;
   b) working the object to a final shape;
   c) sintering the object at a temperature of 1300 to 1600° C. to transfer zirconium oxide into a tetragonal crystalline structure; and
   d) etching the etchable medium using hydrofluoric acid to remove the etchable medium and impart a micromechanical retention surface.

17. The process of claim 16, wherein the hydrofluoric acid etching step d) imparts pits and micro-lacunas on the surface.

18. The process of claim 16, wherein the hydrofluoric acid in the etching step d) is at a concentration of about 5-15% and the etching medium is contacted with the hydrofluoric acid for a time period of about 1 to 10 minutes.

19. The process of claim 16, wherein the glass particles of the compacting step a) have about 1 to about 40 μm average diameter size.

20. A process for manufacturing a zirconium dioxide prosthesis, the zirconium dioxide being stabilized, comprising the steps:
   a) compacting a zirconium dioxide powder and stabilizing oxide of yttrium oxide wherein the compacting is at a pressure of 45 to 150 MPa to form an object and simultaneously impacting an etchable medium into a surface of the object, the etchable medium is glass particles;
   b) working the object to a final shape;
   c) sintering the object at a temperature of 1300 to 1600° C. to transfer zirconium dioxide into a yttria-stabilized tetragonal zirconia or polycrystals (Y-TZP) structure; and
   d) etching the etchable medium using hydrofluoric acid to remove the etchable medium and impart a micromechanical retention surface.

* * * * *